United States Patent

Raff et al.

Patent Number: 5,140,535
Date of Patent: Aug. 18, 1992

[54] PROCESS, USE OF THE SAME AND APPARATUS FOR LAMBDA VALUE DETECTION

[75] Inventors: Lothar Raff, Remseck; Eberhard Schnaibel, Hemmingen; Michael Westerdorf, Möglingen, all of Fed. Rep. of Germany

[73] Assignee: Robert Bosch GmbH, Stuttgart, Fed. Rep. of Germany

[21] Appl. No.: 466,264

[22] PCT Filed: Aug. 18, 1988

[86] PCT No.: PCT/DE88/00504
§ 371 Date: Feb. 20, 1990
§ 102(e) Date: Feb. 20, 1990

[87] PCT Pub. No.: WO89/01623
PCT Pub. Date: Feb. 23, 1989

[30] Foreign Application Priority Data

Aug. 19, 1987 [DE] Fed. Rep. of Germany ....... 3727573

[51] Int. Cl.⁵ ............................................. F02B 3/00
[52] U.S. Cl. ................................. 364/571.07; 364/573; 364/431.06; 123/694
[58] Field of Search .................. 364/571.01, 571.02, 364/571.03, 571.04, 571.07, 577, 431.05, 431.06, 573; 123/440, 489; 204/425, 426, 424; 73/23.21, 23.31, 23.32

[56] References Cited

U.S. PATENT DOCUMENTS

| | | | |
|---|---|---|---|
| 4,187,806 | 2/1980 | Schnurle et al. | 123/440 |
| 4,208,993 | 6/1980 | Peter | 123/440 |
| 4,223,644 | 9/1980 | Latsch et al. | 123/440 |
| 4,393,841 | 7/1983 | Drews et al. | 123/440 |
| 4,492,205 | 1/1985 | Jundt et al. | 123/440 |
| 4,528,957 | 7/1985 | Jundt et al. | 123/440 |
| 4,742,808 | 5/1988 | Blümel et al. | 123/440 |
| 4,768,485 | 9/1988 | Brandner et al. | 123/440 |
| 4,901,240 | 2/1990 | Schmidt et al. | 364/431.06 |

Primary Examiner—Parshotam S. Lall
Assistant Examiner—Michael J. Zanelli
Attorney, Agent, or Firm—Walter Ottesen

[57] ABSTRACT

In a method for lambda value detection, the voltages of the loaded and the unloaded lambda sensor are detected and the internal resistance of the sensor is calculated from these values with the aid of the known value of the load resistance. The value of the internal resistance and the respective value of the voltage of the sensor in the unloaded state serve as input variables for a characteristic field, in which lambda values dependent on values of the internal resistance and of the voltage of the sensor in the unloaded state are stored. The method of the invention affords the advantage that lambda values can be measured very accurately even in the strongly temperature-dependent rich branch of a sensor, for example, of a sensor of the Nernst type. The values thus detected can be indicated by a measuring device or they can be used for exhaust gas control, for example in warming-up or at full load.

13 Claims, 3 Drawing Sheets

PROCESS, USE OF THE SAME AND APPARATUS FOR LAMBDA VALUE DETECTION

FIELD OF THE INVENTION

The invention relates to a method for the detection of the lambda value as it is supplied by a lambda sensor. The lambda sensor is arranged, for example, in the exhaust gas stream of an internal combustion engine The invention also relates to uses of such a method and an apparatus for carrying out the method.

BACKGROUND OF THE INVENTION

The value of the voltage supplied by a lambda sensor depends not only on the lambda value at the location of the sensor, but also on its temperature. The dependence is particularly strong in the rich branch. Due to the temperature response, the measured results are falsified to such an extent that, below a certain temperature, the voltages supplied by the sensor cannot be utilized at all for control. The internal resistance of the sensor, for example, is measured, which decreases with increasing temperature, in order to detect the cut-in threshold from which the values are used.

A method for internal resistance measurement is described in U.S. Pat. No. 4,742,808. The sensor voltage is measured once in the unloaded state and then under load by a load resistor with a predetermined resistance value. From the two voltages and the known resistance value, the actual internal resistance is calculated. This is compared with a threshold value, and then, if the actual value is below the threshold value, the voltage values are used for lambda control.

A simpler method, in which the temperature dependence of the internal resistance is utilized, is known from U.S. Pat. No. 4,528,957, but this method does not make it necessary to work out specifically the internal resistance. The known method uses the fact that the voltage picked off at a load resistor lying in series with the sensor does not only change whenever the sensor voltage changes due to lambda value fluctuations, but that the voltage also changes whenever the internal resistance changes. It is therefore not necessary at all to work out the internal resistance with the aid of the load resistor; instead, it is sufficient to compare the voltage picked off at the load resistor with a voltage threshold value in order to detect the sensor readiness. Actually, two thresholds are necessary, since two different voltages can be supplied with the same internal resistance, dependent on whether the sensor is just then supplied with exhaust gas which derives from the rich mixture or from the lean mixture.

In the case of the above-mentioned methods for sensor-readiness detection, the threshold values are set such that control readiness of the sensor is only detected when the internal resistance is only changing slightly and consequently hardly falsifies the measured result any longer.

An arrangement is known from EP-A3-0 152 293 which considers the internal resistance of a limit current sensor when determining a lambda value from a current flowing through the limit current sensor.

The invention is based on the object of specifying a method for lambda value detection by means of a lambda sensor, which supplies a voltage dependent upon the oxygen content to be measured, which method operates reliably even at lower temperatures than before. The invention is furthermore based on the object of specifying uses for this method. Finally, the invention is based on the object of providing an apparatus for carrying out such a method.

SUMMARY OF THE INVENTION

The method according to the invention is characterized in that the internal resistance of the sensor is determined and allowance is made for the internal resistance when the lambda value is determined from the sensor voltage. For this purpose, either the measured sensor voltage can be corrected with the aid of the internal resistance and then the lambda value be determined from the corrected voltage, or the lambda value can be determined from the measured sensor voltage and this value is corrected with the aid of the internal resistance. It is particularly advantageous to determine the lambda value from a lambda value sensor voltage internal resistance characteristic field with the sensor voltage being the voltage of the sensor in the unloaded state.

The internal resistance can be determined with simple structural measures with the aid of a load resistor. Particularly quick measurements can be obtained when a predetermined external voltage is applied to the sensor and the internal resistance is calculated from this voltage and the flowing current.

When in use for lambda control, the method according to the invention supplies better control results and, when in use in a measuring device, it provides more reliable measured results than previous methods. For these uses, it is of advantage if it is possible to operate in a wide temperature range. In order to make this possible, an advantageous further development of the method for lambda value detection provides that the loading takes place by a load resistor having resistances of different resistance values, depending on the particular internal resistance of the sensor, that is, depending on the particular temperature range. The value of the load resistance is chosen in each case such that the sensor is not excessively loaded so that it is not damaged. Of significance in particular for the use for control is a further development which provides that the value of the load resistance is chosen such that the voltage of the again unloaded sensor is substantially recovered by the time of the next sampling.

The method according to the invention can be used in the entire operating range of a sensor, that is from lean into rich. However, since the temperature dependence in the lean range and in the range around lambda $=1$ is relatively small, an advantageous further development of the uses provides that in these ranges the conversion of voltage values to lambda values takes place linearly without allowance for a temperature dependence.

The apparatus according to the invention for lambda value detection includes: a means for detecting the voltage of the unloaded sensor; a means for determining the internal resistance of the sensor; and, in addition, a characteristic field, for reading-out a lambda value associated with the measured voltage values.

BRIEF DESCRIPTION OF THE DRAWINGS

The invention is explained in more detail below with reference to exemplary embodiments illustrated by figures, in which.

DESCRIPTION OF THE PREFERRED EMBODIMENTS OF THE INVENTION

The proposed method, the uses thereof and the apparatus for carrying out the method make the intensely temperature-dependent rich branch and the less temperature-dependent lean branch of lambda sensors, in particular those of the Nernst type (without and with heating), usable with little effort. This is based on the fact that there is a clearly reproducible relationship between the sensor voltage $U_S$, the sensor temperature $T_S$ and lambda. The lambda value at the particular operating point is interpolated from a characteristic field of the corresponding lambda sensor. The characteristic field is set up over the variables $U_S$ and $T_S$ and this method consequently allows a lambda determination from $U_S$ and $T_S$. Since the internal resistance $R_i$ of the oxygen sensor is, in turn, a function of the temperature $T_S$ of this resistance, it is also possible to alternatively use a characteristic field set up over $U_S$ and $R_i$ of the oxygen sensor for determining the lambda value. The method provides that, in a first step, the sensor voltage $U_S$ is determined under negligible load as idling voltage and that, in a second step, the sensor voltage $U_L$ of the oxygen sensor loaded with a precision resistor $R_L$ is measured and the internal resistance $R_i$ is determined by means of a simple arithmetic routine.

Figure 1:
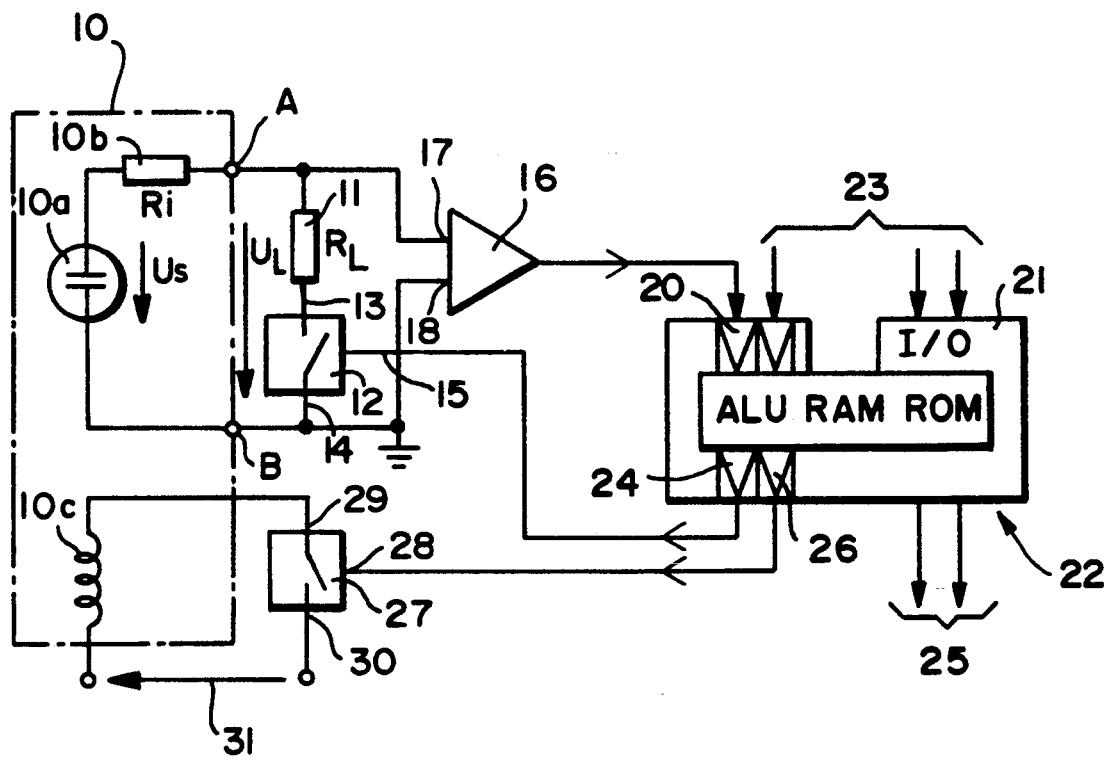
FIG. 1 shows a block circuit diagram of an apparatus according to the invention.

An apparatus and the method which can be carried out with this apparatus are now explained in more detail with reference to the block circuit diagram of FIG. 1. 10 identifies the lambda sensor, which includes: the sensor original voltage source ($U_S$) 10a; the temperature-dependent internal resistance ($R_i$) 10b of the same; and, if the lambda sensor is to be heated, an electric heating element 10c. With this heating element 10c the sensor can be heated up, if need be, to a usual operating temperature of 600° C. to 800° C. The output terminals A and B of the sensor lead to the two inputs 17 and 18 of a differential amplifier 16 with very high internal resistance. One of the two input terminals of this amplifier, here the terminal 18, is preferably connected to the vehicle ground. An electrically triggerable switch 12 lies between the output terminals A and B. The one switching section 13 of the switch 12 is connected via a load resistor 11 of the resistance value $R_L$ to the output terminal A, and the other switching section 14 of the switch 12 is connected to the one input of the amplifier 16 and to the vehicle ground. The output of the amplifier 16, which preferably has, due to a strong negative feedback, only low, but virtually constant gain, is led to an analog/digital (A/D) input channel 20 of an input/output (I/0) interface 21 of a microcomputer 22; the large I/0 interface 21 generally has further A/D inputs 23 as well. An output channel 24 of the microcomputer 22 is connected to the control electrode 15 of the electric switch 12. A further output channel 26 is connected to a corresponding control electrode 28 of an electric switch 27. The switching sections 29 and 30 of the switch 27 are connected in series with the heating element 10c and are connected to a supply voltage 31. If the heating element is omitted, the other circuit components just mentioned are also omitted. The I/0 interface 21 of the microcomputer 22 generally has further connections 25 as well for the triggering of consumers.

The sensor voltage $U_S$ is then sampled regularly in short periodic succession, in practice about every 10 ms, that is, it is read via the A/D input channel 20 into the microcomputer 22 and further processed and evaluated there. The exemplary sampling frequency resulting, in the order of magnitude of 100 Hz, ensures both a still adequate time resolution of the signal of the lambda sensor and a still adequate cut-off frequency of a correspondingly designed exhaust gas control circuit, if the sensor signal serves for such a control. In order not to noticeably impair the dynamic response of a controller contained therein, the "test loading" of the lambda sensor with the load resistance $R_L$ takes place during a time interval between two successive time points of the regular sampling time points mentioned above, that is, during a period of <10 ms, for example, 5 ms. In order not to allow memory effects (temperature-dependent falsification of the sensor characteristic by a previous high current load) of the lambda sensor to act to a disturbing extent, the time interval between the individual test loads of the lambda sensor is considerably greater, for example, it is chosen in the order of magnitude of 1 s, thereby producing a repetition frequency of the test loads of ½ Hz. Consequently, for example, a load ratio of >1/200 is established, and accordingly a desirably low average value of the current taken from the sensor, so that its current aging remains low.

The determination of the temperature-variable internal resistance $R_i$ of the lambda sensor takes place in such a way that two voltages $U_L$ and $U_S$ detected at the interval of two regular sampling time points, for example, at the interval of 10 ms, are combined by a computer program according to the following formula:

$$R_i = R_L(U_S - U_L)/U_L \tag{1}$$

In this case, the sensor voltage $U_L$ under load and the directly following measured idling voltage $U_S$ are considered approximately as "simultaneous". This is permissible due to the much greater thermal time constant of the lambda sensor in comparison with the regular sampling period.

The calculated internal resistance $R_i$ of the sensor serves as a parameter in a characteristic field, in which lambda values are stored in dependence on the measured unloaded sensor voltage $U_S$. Such a lambda characteristic field is shown schematically in FIG. 2. If the measured internal resistance lies between two stored characteristics, an interpolation takes place. This is carried out periodically during each sampling period between two regular detections of the unloaded sensor voltage $U_S$; that is, it is carried out with the last-determined internal resistance value as correction value entered into the characteristic field up to the next determination, which took place once again, for example, after 1 s at the latest, of the then current sensor internal resistance as new characteristic field input correction value. By this measure it is achieved that the microcomputer, as an essential component of an exhaust gas control circuit, is only slightly loaded by the determination of interpolation values to update the internal resistance and consequently by the correction of the sensor voltage. Nevertheless, an adequately rapid updating of the sensor characteristic, adapted to the thermal time constant of the lambda sensor, takes place with respect to a lambda value of the exhaust gas to be adjusted.

Figure 2:
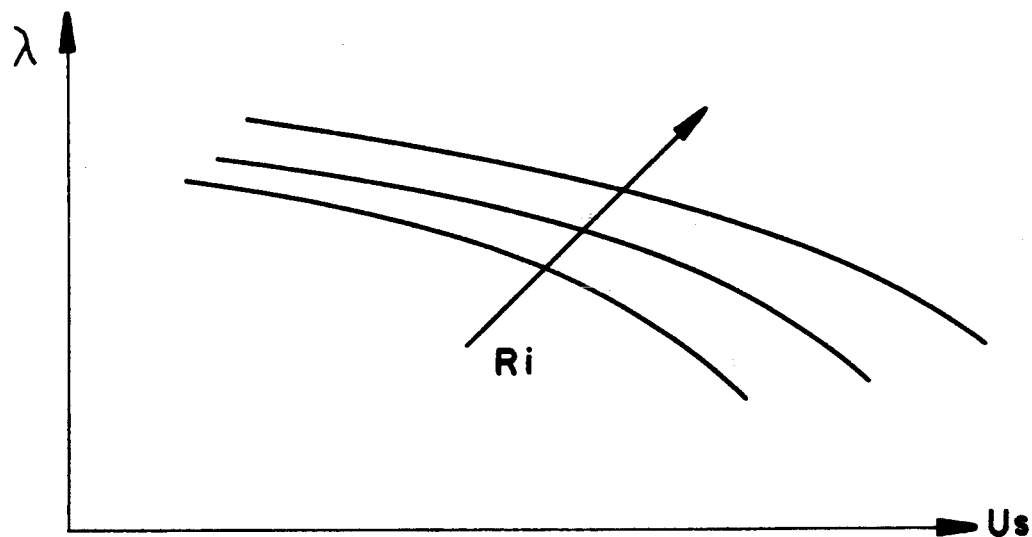
FIG. 2 shows a characteristic field in schematic representation for the entire lambda range.
Figure 3:
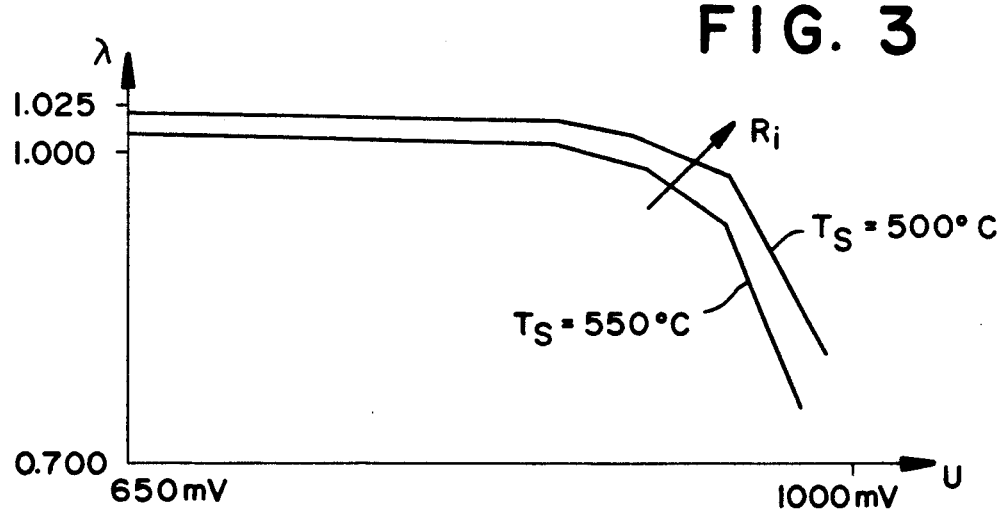
FIGS. 3 and 4 show each a characteristic field for the rich range, that is, for the range of relatively low sensor temperatures and for the range of relatively high sensor temperatures, respectively.
Figure 4:
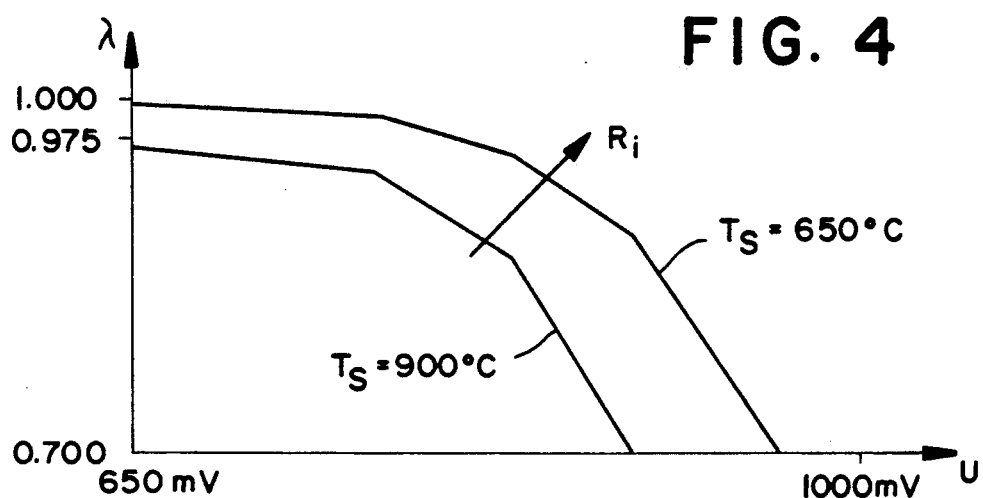

While FIG. 2 is a schematic representation of a characteristic field for the entire lambda range, FIGS. 3 and 4 represent specific diagrams of characteristic fields for the rich lambda range for two different temperature ranges. As can be seen from FIG. 3, at low temperatures, that is, at temperatures between 500° C. and 550° C. in the case shown, the lambda values change only slightly as a function of the internal resistance. By contrast, at the high temperatures according to the diagram of FIG. 4, that is at temperatures between 650° C. and 900° C. in the case of the example, the fluctuations are considerable. Thus, a voltage $U_S$ of 860 mV, measured with the unloaded sensor, corresponds at 900° C. to a lambda value of approximately 0.75, while at a sensor temperature of 650° C. it corresponds approximately to a lambda value of 0.95. This makes it clear that the method of the invention not only makes it possible to determine reliable lambda values at lower temperatures than previously, but that it is also capable of supplying more accurate measuring results than previously in a temperature range in which there was sensor readiness even according to conventional concepts The method consequently makes it possible to provide constant control even in the rich range, that is, for warm-up or full-load control. In addition, the lambda detection described can be used to advantage with a lambda measuring device.

It is pointed out that only two characteristics for different internal resistances are plotted in FIGS. 3 and 4. In practice, more characteristics will be used, in particular in the higher temperature range, in which the variation is great, in order not to allow interpolation errors to become too great. Also, as many support points as possible along the abscissa will be used. The limits for the number of support points and the number of characteristics per characteristic field are set by the capacity of the characteristic field memory used.

Figure 5:
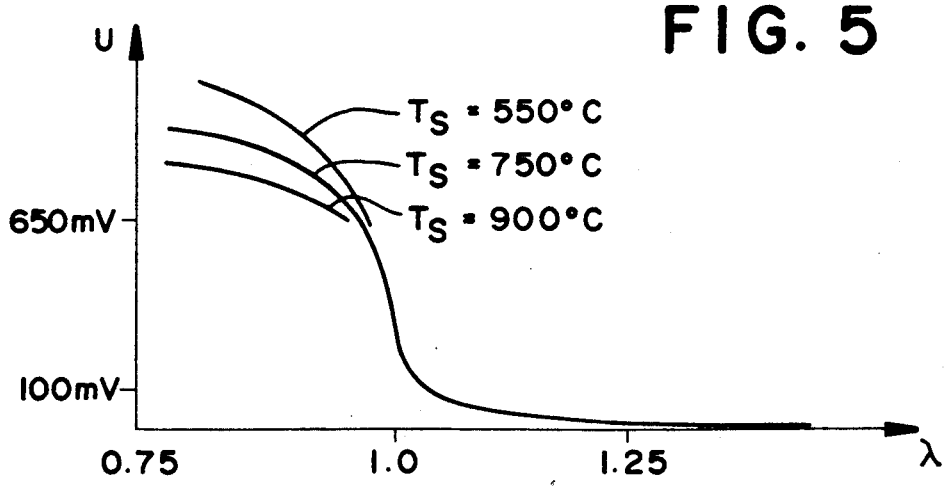
FIG. 5 shows a diagram to explain different detection ranges for lambda values; and, FIG. 6 shows a block circuit diagram to explain applications in which a lambda value detection plays a part while considering the internal resistance of the lambda sensor.

In FIG. 5, sensor characteristics for various sensor temperatures are drawn. In the representation, the lambda values run along the abscissa and the voltage values of the unloaded sensor run along the ordinate, that is precisely in the opposite to the representations according to FIGS. 2 to 4. The characteristics are subdivided into three regions, that is, into an upper voltage range above approximately 650 mV for rich lambda values, a lower range below approximately 100 mV for lean lambda values and an intermediate range for controlling to lambda = 1. In the lower and middle ranges, there is only low temperature dependence of the characteristics. For this reason, the characteristics are represented by a single characteristic in each case in the respective range. In the upper range, on the other hand, the previously described characteristic fields for different temperature ranges are used.

Figure 6:
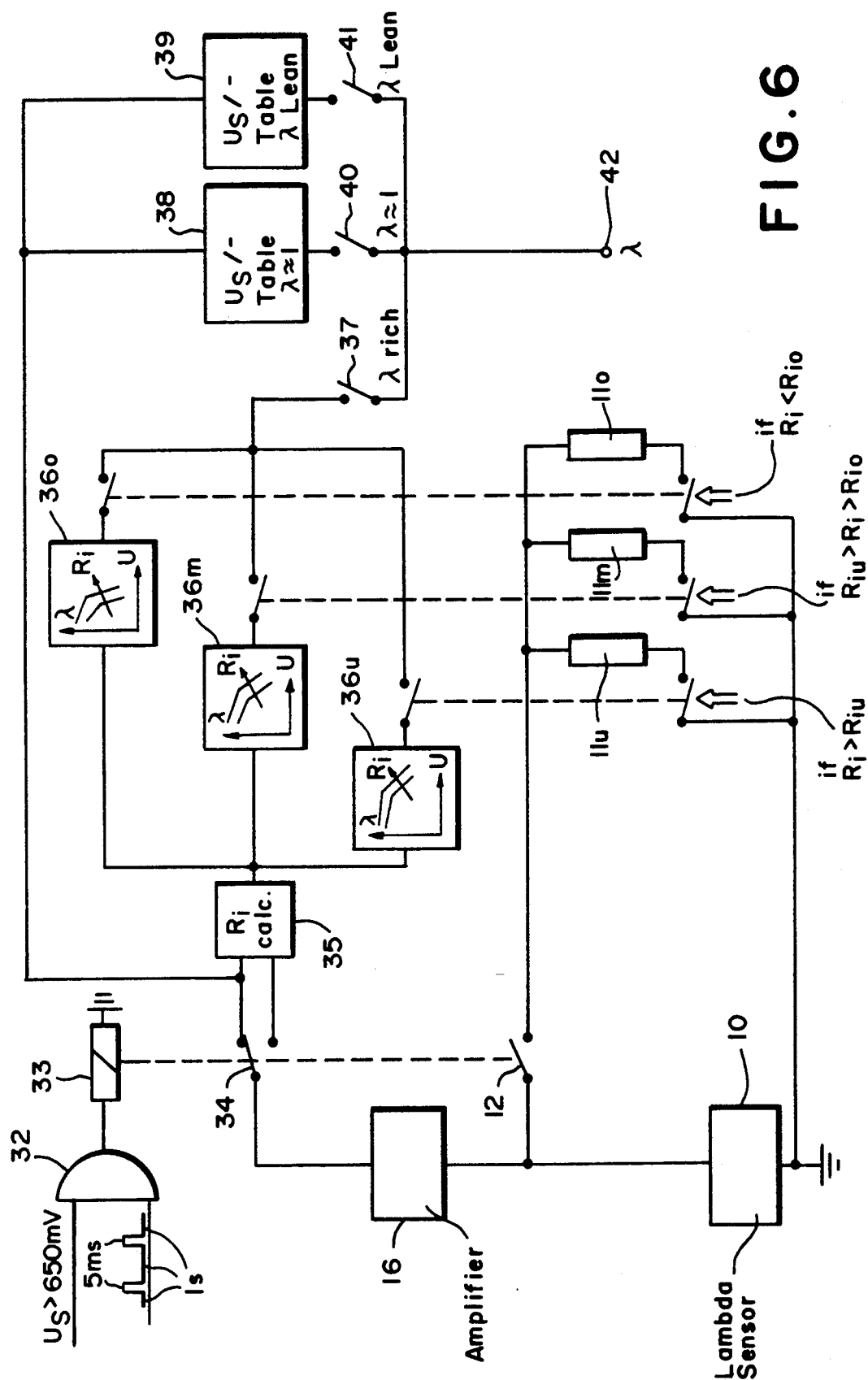

A function diagram for a detection device for lambda values, which uses a characteristic division according to FIG. 5, is illustrated in FIG. 6 and is explained below.

The sensor 10 included in FIG. 6 can be loaded with one of three load resistors 11o, 11m or 11u, depending on whether the internal resistance $R_i$ has a value $R_{io}$ for an upper temperature range, $R_{im}$ for a middle temperature range or $R_{iu}$ for a lower temperature range. The load resistors in the exemplary embodiment have resistances of 500 ohms, 2000 ohms and 5000 ohms for the upper, middle and lower temperature ranges, respectively. These resistances are, however, only cut in to the lambda sensor 10 if the sensor voltage is in the upper range of the characteristic according to FIG. 5, that is higher than 650 mV. This condition is shown in FIG. 6 as input condition and an AND element 32. A clock voltage is fed to the other input of the AND element and the clock voltage is determined by a signal which has high level for 5 ms and then low level for 1 s. The switch 12 for the cutting-in of the load resistors is consequently closed by a switch trigger 33 every 1 s for 5 ms when the sensor voltage is above 650 mV. As already explained with reference to FIG. 1, the switch trigger is part of the microcomputer 22.

The voltage picked off at the sensor 10 is amplified by the amplifier 16 and supplied via a voltage switch 34 to a calculation means 35. The voltage switch 34 is switched together with the load resistor switch 12. With a cut-in load, the calculation means 35 consequently receives the voltage $U_L$ determined under load, while it otherwise receives the voltage $U_S$ of the unloaded sensors. From these values, the calculation means 35 calculates according to equation (1) explained above the internal resistance $R_i$ of the sensor. Depending on the value of the internal resistance, one of the load resistors 11o, 11m or 11u of the sensor 10 is cut in. Likewise dependent on this value, one of three characteristic fields is switched to a rich switch 37. The three characteristic fields 36o, 36m and 36u correspond, in turn, to upper, medium and lower temperature ranges. The characteristic field 36u thus corresponds to the characteristic field according to FIG. 3, while the characteristic field 36o corresponds to the characteristic field of FIG. 4.

The voltage $U_S$ of the unloaded sensor is not only fed to the calculation means 35 and to the characteristic fields 36.i, but also to a linearization table 38 for lambda = 1 and to a lean linearization table 39. These tables perform the linearizations explained with reference to FIG. 5. Their output values are passed to a switch 40 for values around lambda = 1 or to a lean switch 41. The rich switch 37, the switch 40 for values of lambda around 1 and the lean switch 41 are connected to the output 42 of the apparatus for lambda value detection according to FIG. 6. Which of the three switches is closed depends on the voltage value $U_S$ of the unloaded sensor. At voltages of above 650 mV, the rich switch 37 is closed, at voltages below 100 mV, the lean switch 41 is closed, and at voltages in between, the switch 40 for values around lambda = 1 is closed.

The apparatus consequently emits values from the lean linearization table 39 at voltages below 100 mV, whereas it emits lambda values from the linearization table 38 for lambda = 1 at voltages between 100 mV and 650 mV and values from the characteristic fields 36.i for voltages above 650 mV, depending on which temperature range, that is which internal resistance range, is present at the time The function blocks of the apparatus according to FIG. 6 are integrated as far as possible into the microcomputer 22 according to FIG. 1.

As explained above, the sensor is loaded only every 1 s for 5 ms. The unloaded sensor, on the other hand, is sampled every 10 ms. This means that the sensor voltage must recover relatively quickly after loading, in order that the measured value for the next sampling of the voltage of the unloaded sensor is not falsified by the previous loading. The requirement of quick recovery is made possible by different load resistances being chosen for various internal resistance ranges, that is, higher load resistances are chosen the higher the internal resistance. The number of load resistance ranges to be used thus depends on the rate of recovery of the sensor and on the sampling rate. Consequently, more or less ranges than in the exemplary embodiment may be used, that is, more or less than three ranges.

The internal resistance calculation does not necessarily have to be performed in accordance with equation (1) specified above, but depends on the wiring of the sensor. Thus, the determination of the internal resistance may be performed with any load networks, that is, with such networks as are described in U.S. Pat. No. 4,742,808.

In the exemplary embodiment, a lambda value detection is carried out with allowance for the sensor internal resistance only for the range of rich lambda values. This has to do with the type of sensor used, which only has low temperature dependence in the lean range. As already mentioned above, the method described may, however, be used in all measuring ranges.

Of great advantage in the embodiment of the invention is the simple design which, apart from the microcomputer, which is available in any case, only requires the load resistor 11 and the switch 12 in order to be able to determine the internal resistance. However, the voltage of the unloaded sensor is measured inaccurately whenever it is sampled if the sensor has not yet fully recovered from a load. It is also to be considered that the voltages $U_S$ and $U_L$ in the unloaded state and loaded state are not measured simultaneously but one after the other and are only considered as measured simultaneously. This procedure is quite unproblematical in the lean and rich lambda value ranges, since in these ranges the sensor voltages do not change considerably within the measuring time interval. In the range around lambda=1, however, considerable voltage jumps can occur in the small time interval between the two measurements if a sensor with a pronounced jump behavior is used.

The time problems are eliminated if the internal resistance of the sensor is determined not by loading the sensor but if it is determined separately. This is achieved by applying a given voltage to the sensor, by measuring the current flowing through the sensor and by calculating the internal resistance from the given voltage and the measured current. An alternating voltage, for example, of 2000 Hz, is preferably used as voltage. The flowing alternating current can easily be separated from the current induced by the sensor electromotor force and is then evaluated. The internal resistance determination according to this method can be performed at intervals of just a few seconds, for example, 2 s. This is because the sensor internal resistance changes only relatively slowly. The sensor voltage of the unloaded sensor is, on the other hand, sampled much more frequently, for example, every 10 ms. The measured sensor voltage is in no event falsified by a previous loading.

The same applies if an alternating current with known root-mean-square value is sent through the sensor, the root-mean-square voltage at the sensor or at an auxiliary resistor is measured and the internal resistance of the sensor is calculated from current and voltage.

In the exemplary embodiment, it has been assumed that the lambda value is read out from a characteristic field. This procedure has the advantage of low computer loading. Theoretically, however, it is just as possible to correct the measured sensor voltage with the aid of a mathematical function with allowance for the internal resistance. The mathematical function in this case expresses the relationship between the internal resistance and the sensor voltage. Accordingly, it is also possible to determine initially the lambda value from the measured sensor voltage in the unloaded state of the sensor and to correct this value with the aid of a mathematical function. In this case, the function represents the relationship between lambda value and internal resistance.

We claim:

1. A method for detecting a value of lambda with the aid of a lambda sensor having a sensor voltage $U_S$ thereacross when unloaded, the lambda sensor having an internal resistance $R_i$ which varies as a function of lambda sensor temperature $T_S$, the method comprising the steps of:

detecting the sensor voltage $U_S$;

determining the internal resistance $R_i$ of said lambda sensor by loading the sensor at time intervals with a load resistance having a value which becomes less with decreasing internal resistance $R_i$; measuring the voltage $U_L$ of the loaded sensor and calculating the internal resistance from the load resistance value and the voltages $U_S$ and $U_L$ of the unloaded and loaded sensor, respectively;

providing a characteristic field wherein lambda values are stored as a function of said sensor voltage $U_S$ with said internal resistance $R_i$ being a parameter in said field;

addressing said characteristic field with respective values of said sensor voltage $U_S$ and internal resistance $R_i$; and, reading out a value of lambda from said characteristic field corresponding to said sensor voltage $U_S$ and internal resistance $R_i$.

2. The method of claim 1, wherein: the reduction of the load resistance takes place by cutting in different resistors with predetermined resistance values.

3. The method of claim 2, wherein: the respective value of the load resistance is chosen such that the voltage of the again unloaded sensor substantially recovers by the time of the next sampling.

4. The method of claim 2, wherein: the method is used for lambda value detection for a lambda indicating device for indicating in the rich range; and, characteristic fields (36u, 36m, 36o) are assigned to the load resistors (11u, 11m, 11o), respectively.

5. The method of claim 1, wherein: the method is used for lambda value detection for a lambda control in the rich lambda range.

6. The method of claim 5, wherein: the lambda range is around 1 and/or in the lean lambda range, and the lambda value detection is performed by linear conversion of the particular measured sensor voltage $U_S$ without loading into a lambda value.

7. The method of claim 1, wherein said characteristic field includes a family of curves for different values of sensor temperature; and, said value of lambda is read out after interpolation between said curves.

8. The method of claim 1, wherein: for the determination of the internal resistance $R_i$, a known current is applied to the sensor and the voltage across the sensor is measured and the internal resistance $R_i$ is calculated from the known current and the voltage measured across the sensor.

9. The method of claim 1 wherein: the particular value of the load resistance is chosen such that the voltage of the again unloaded sensor substantially recovers by the time of the next sampling.

10. The method of claim 1, the method comprising the further steps of monitoring said sensor voltage and applying said sensor voltage to said characteristic field when said sensor voltage exceeds a predetermined level indicative of rich operation and applying said sensor voltage to a linearization table when said sensor voltage drops below said predetermined level indicative of not rich or lean operation.

11. A method for detecting a value of lambda with the aid of a lambda sensor having a sensor voltage $U_S$ thereacross when unloaded, the lambda sensor having an internal resistance $R_i$ which varies as a function of lambda sensor temperature $T_S$, the method comprising the steps of:

detecting the sensor voltage $U_S$;

determining the internal resistance $R_i$ of said lambda sensor;

providing a characteristic field wherein lambda values are stored as a function of said sensor voltage $U_S$ with said internal resistance $R_i$ being a parameter in said field;

addressing said characteristic field with respective values of said sensor voltage $U_S$ and internal resistance $R_i$;

reading out a value of lambda from said characteristic field corresponding to said sensor voltage $U_S$ and internal resistance $R_i$; and, monitoring said sensor voltage and applying said sensor voltage to said characteristic field when said sensor voltage exceeds a predetermined level indicative of rich operation and applying said sensor voltage to a linearization table when said sensor voltage drops below said predetermined level indicative of not rich or lean operation.

12. A method for detecting a value of lambda with the aid of a lambda sensor having a sensor voltage $U_S$ thereacross when unloaded, the lambda sensor having an internal resistance $R_i$ which varies as a function of lambda sensor temperature $T_S$, the method comprising the steps of:

detecting the sensor voltage $U_S$;

determining the internal resistance $R_i$ of said lambda sensor by applying a given voltage to said sensor and measuring the current flowing through said sensor; and, then calculating the internal resistance from said given voltage and said measured current;

providing a characteristic field wherein lambda values are stored as a function of said sensor voltage $U_S$ with said internal resistance $R_i$ being a parameter in said field;

addressing said characteristic field with respective values of said sensor voltage $U_S$ and internal resistance $R_i$;

reading out a value of lambda from said characteristic field corresponding to said sensor voltage $U_S$ and internal resistance $R_i$;

monitoring said sensor voltage and applying said sensor voltage to said characteristic field when said sensor voltage exceeds a predetermined level indicative of rich operation; and, applying said sensor voltage to a linearization table when said sensor voltage drops below said predetermined level indicative of not rich or lean operation.

13. The method of claim 12, wherein said linearization table is provided for $\lambda \approx 1$ range and a further linearization table is provided for the lean range.

* * * * *